(12) United States Patent
Fredriksen

(10) Patent No.: US 6,210,336 B1
(45) Date of Patent: Apr. 3, 2001

(54) DAMPING CUSHION FOR ULTRASOUND PROBES

(75) Inventor: Paul Sverre Fredriksen, Tolvsroed (NO)

(73) Assignee: G.E. Vingmed Ultrasound A/S, Horten (NO)

(*) Notice: Subject to any disclaimer, the term of this patent is extended or adjusted under 35 U.S.C. 154(b) by 0 days.

(21) Appl. No.: 09/324,811

(22) Filed: Jun. 2, 1999

Related U.S. Application Data (63) Continuation-in-part of application No. 09/223,403, filed on Dec. 30, 1998, now Pat. No. 6,139,502.

(51) Int. Cl.⁷ .......................................... A61B 8/00
(52) U.S. Cl. ............................................... 600/459
(58) Field of Search ................... 600/437, 459, 600/472; 73/633, 642, 644

(56) References Cited

U.S. PATENT DOCUMENTS

| | | |
|---|---|---|
| D. 369,307 | 4/1996 | Imling et al. . |
| 4,059,098 * | 11/1977 | Murdock .................. 600/437 |
| 4,579,123 * | 4/1986 | Chen et al. ................. 73/644 |
| 4,593,699 * | 6/1986 | Poney et al. .............. 600/459 |
| 4,603,701 * | 8/1986 | Chen ......................... 73/644 |
| 4,688,578 * | 8/1987 | Takano et al. ............. 600/459 |
| 4,796,632 * | 1/1989 | Boyd et al. ............... 600/459 |
| 5,299,578 | 4/1994 | Rotteveel et al. . |
| 5,351,691 | 10/1994 | Brommersma . |
| 5,381,795 | 1/1995 | Nordgren et al. . |
| 5,482,047 | 1/1996 | Nordgren et al. . |

FOREIGN PATENT DOCUMENTS

| | | |
|---|---|---|
| 3337 842 A1 | 4/1984 | (DE) . |
| 0 120 410 A2 | 10/1984 | (EP) . |
| 0 146 049 A2 | 6/1985 | (EP) . |

* cited by examiner

Primary Examiner—Francis J. Jaworski
(74) Attorney, Agent, or Firm—McAndrews, Held & Malloy, Ltd.

(57) ABSTRACT

An ultrasonic probe is provided. The probe includes a base member and an ultrasonic transducer housed by the base member. The probe also includes an intermediary damping member secured to the base member. The damping member includes an interior cavity for receiving an acoustic coupling fluid. The probe may optionally be secured to a flexible intermediary buffer. In an alternative embodiment, a coupling member is secured to the base member. The coupling member includes an interior cavity for receiving an acoustic coupling fluid. The coupling member also includes a malleable contacting surface for contacting an anatomical structure during use. Another alternative embodiment of the invention includes a transducer housing, an ultrasonic transducer mounted in the housing, and a flexible cushioned pad directly secured to a periphery of the transducer housing. Yet another alternative embodiment includes a pliable damping member defining an interior for retaining a fluid and structure for secured the damping member to an ultrasonic probe.

39 Claims, 10 Drawing Sheets

DAMPING CUSHION FOR ULTRASOUND PROBES

CROSS-REFERENCE TO RELATED APPLICATIONS

This application is a continuation-in-part of Application No. 09/223,403, filed Dec. 30, 1998 and issued as U.S. Pat. No. 6,139,502 on Oct. 31, 2000.

BACKGROUND OF THE INVENTION

The present invention generally relates to ultrasound probes and in particular to ultrasound probe and handle housings and cushions for use with ultrasound probes.

Ultrasonic diagnostic imaging probes generally have been used in the past to image anatomical structures within the body. Ultrasonic probes have been used in the past during non-invasive procedures (such as trans-thoracic probes), during invasive procedures (such as trans-esophageal echocardiography (TEE) probes and trans-vaginal probes), and during surgical procedures (i.e., intraoperative probes).

When using ultrasonic probes, it is important that the hand of the physician using the probe not obscure the site being examined. While the probe is imaging, for example, a physician must be able to accurately determine and maintain the position of the probe while looking at a monitor displaying the information obtained from the probe.

Past intraoperative ultrasound probes have provided, for example in U.S. Pat. No. 5,381,795 to Nordgren et al., an intraoperative ultrasound probe having a transducer section and an angled handle section that form an obtuse angle with respect to one another. The shape of the handle was used in an attempt to permit the physician to grasp the probe without blocking the physician's view of the surgical site. Surgical procedures in which intraoperative probes have been used include vascular surgery and transplant surgery. During vascular surgery, ultrasonic imaging probes can be used to image and diagnose the interior of carotid arteries. In transplant surgery, intraoperative ultrasonic probes can be used to verify successful attachment and function of renal arteries. Intraoperative ultrasound probes are preferably small and as easy to manipulate as surgical instruments.

Past trans-vaginal probes have provided, for example in U.S. Pat. No. 4,742,829 to Law et al., a handle offset from the central axis of the probe. The shape of the handle was used in an attempt to free the space around the entrance of a needle guide to thereby permit manipulation of the needle by hand. The probes disclosed in the above-referenced patents did not, however, present a probe having a multiple-angled handle section.

Past TEE probes have provided, for example in U.S. Pat. No. 5,351,691 to Brommersma, a flexible tube having at one end a probe head. The flexible end part is connected to a housing to allow a probe head to be bent forwards or backwards.

Several problems exist with respect to past ultrasound probes. During examination of organs within the body, particularly during intraoperative examination, the quality of ultrasound images is adversely affected by the presence of a moving organ, due to, for example, blood pulsation. For example, an ultrasound probe may be placed directly on a heart during open heart surgery. The pulsation of the heart applies forces to the ultrasound probe which cause the probe to move up and down and/or side to side and therefore adversely affect the quality of the ultrasound images obtained. The images may be adversely affected because returning ultrasound waves may miss the probe altogether (thereby producing no image) or return when the probe is at a different angle or orientation than when the ultrasound wave was sent (thereby causing an incorrect image to be produced).

Second, ultrasound images are adversely affected by the lack of an effective acoustic coupling due to the fixed (usually flat) transducer or probe surface and the curved or irregular shape of an anatomic structure, such as a heart, artery or other organ (especially during intraoperative examination). When a flat probe is placed against the curved or irregular surface of an anatomic structure, only a portion of the probe actually contacts the anatomic structure. When this occurs, air is located between the non-contacting portion of the probe surface and the anatomic structure. Ultrasonic waves travel at different speeds in air than in the anatomic structure. Because of the different speeds at which ultrasonic waves travel, the ultrasonic waves refract (i.e., bend sharply) when they enter and leave the anatomic structure. Because of this refraction or bending, the returning ultrasound waves may either appear to emanate from an incorrect location or miss the probe altogether. The existence of various, unpredictable air pockets between the probe and anatomic structure may be referred to as the lack of an effective acoustic coupling. A smaller number of air pockets between the probe surface and anatomic structure corresponds to a more effective acoustic coupling.

Third, when using past ultrasound probes, it is difficult to obtain steady probe contact with an organ while not deforming the organ or its blood flow, especially during intraoperative examination. Organ deformation occurs because past ultrasound probes placed a rigid probe surface against the soft organ tissue. In order to achieve an effective acoustic coupling, a probe user may firmly press the probe against the anatomic structure sought to be imaged. This deformation adversely affects ultrasound image quality because an anatomic structure sought to be imaged may be deformed to an unnatural shape or the velocity of blood flow may be altered due to deformation. The alteration of blood flow may be a particular problem where blood flow pattern and/or velocity are sought to be imaged.

Past ultrasound technology has not presented an ultrasonic probe that can avoid the aforementioned problems of organ movement during intraoperative ultrasound examination, the lack of an effective acoustic coupling, and deformation.

A need has long existed for such a probe. A further need remains for an improved ultrasonic probe housing that enables a physician to accurately determine and maintain the position of the probe during use. A need also remains for an improved ultrasonic probe housing that allows the physician to move the probe while maintaining its orientation without having to view the probe to ensure it is oriented properly. It is an object of the present invention to meet these needs.

BRIEF SUMMARY OF THE INVENTION

In an exemplary embodiment of the invention, an ultrasonic probe is provided. The probe includes a base member and an ultrasonic transducer housed by the base member. The probe also includes an intermediary damping member secured to the base member. The damping member includes an interior cavity for receiving an acoustic coupling fluid. The probe may optionally be secured to a flexible intermediary buffer. In another exemplary embodiment of the invention, a coupling member is secured to the base member. The coupling member includes an interior cavity for receiving an acoustic coupling fluid. The coupling member also includes a malleable contacting surface for contacting an anatomical structure during use. An alternative embodiment of the invention includes a transducer housing, an ultrasonic transducer mounted in the housing, and a flexible cushioned pad directly secured to a periphery of the transducer housing. Another alternative embodiment includes a pliable damping member defining an interior for retaining a fluid and structure for secured the damping member to an ultrasonic probe.

DETAILED DESCRIPTION OF THE INVENTION

This application is a continuation-in-part of Application No. 09/233,403, filed Dec. 30, 1998, the subject matter of which is hereby incorporated in its entirety by reference.

Figure 1:
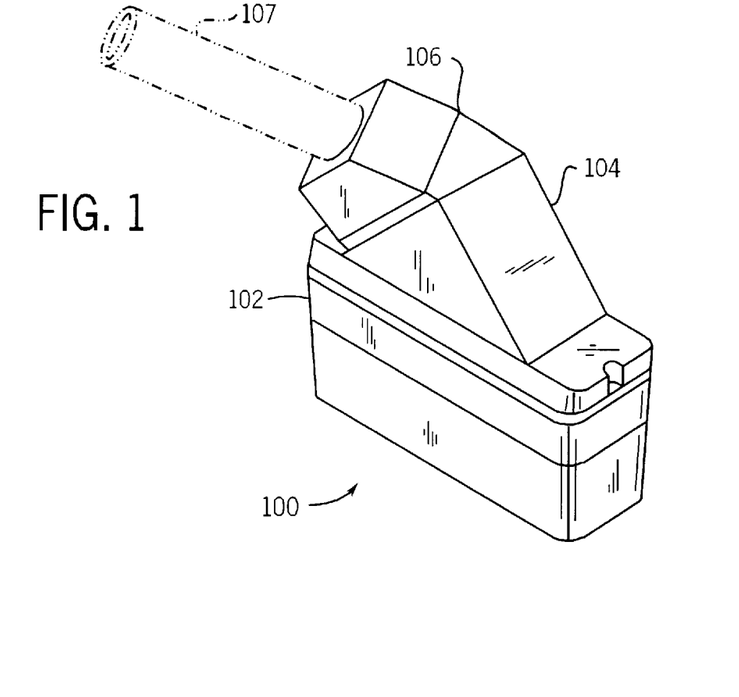
FIG. 1 is a perspective view of a probe and handle housing according to a particular embodiment of the present invention.

FIG. 1 illustrates an ultrasonic probe and handle housing 100. The housing includes a base 102 and a stem extending from the base for handling the probe. The stem includes a first stem portion 104 and a second stem portion 106. A probe cable 107 extends from the second stem portion 106.

Figure 1A:
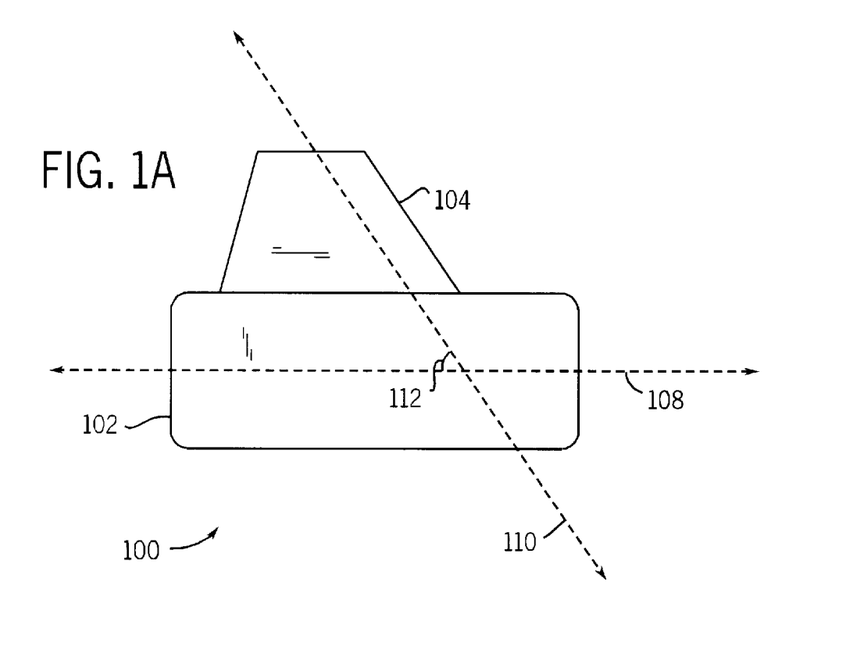
FIG. 1A is a side view of the probe and handle housing, showing the base and first stem portion diagrammatically.

FIG. 1A illustrates a view of the base 102 and first stem portion 104 of the housing 100. The longitudinal axis of the base 108, the longitudinal axis of the first stem portion 110, and the inclined angle 112 at which the two axes intersect are also shown.

Figure 1B:
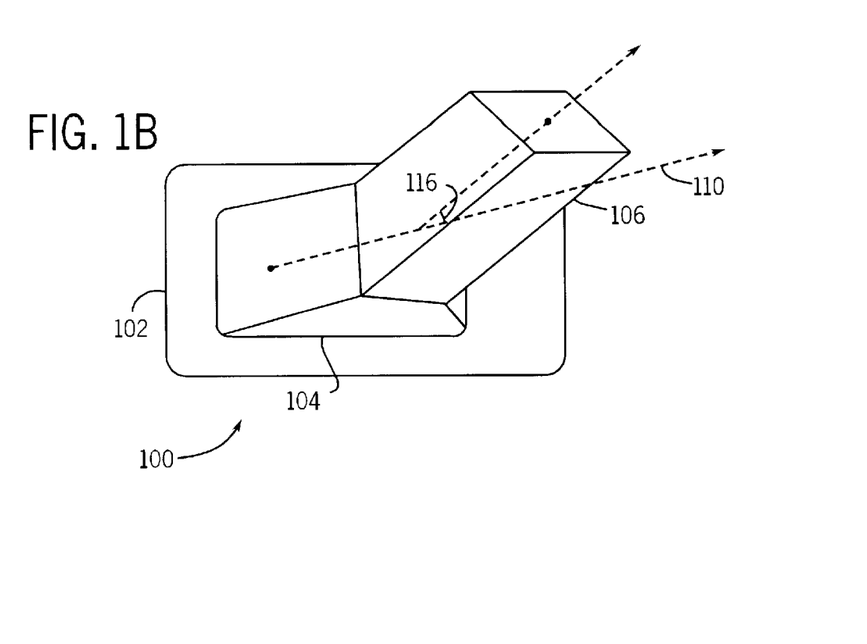
FIG. 1B is a top plan of the probe and handle housing.

Turning to FIG. 1B, a top view of the probe and handle housing 100 is presented. The longitudinal axis along which the first stem portion extends 110, the longitudinal axis along which the second stem portion extends 114, and the angle 116 at which the axes intersect are shown.

Turning back to FIG. 1, a base 102 is provided for use with ultrasonic imaging technology. In the present embodiment, the lower surface of the probe is rectangular in shape, although this is not required. The first stem portion 104 extends from the base 102. The first stem portion 104 may extend from the base 102 in one of several methods such as, for example, the stem portion 104 may be affixed to the base 102 or the stem portion 104 and base 102 may be integrally molded. The first stem portion 104 may extend from the base 102 at any portion of the base 102, including at the center of the upper face of the base 102.

Referring still to FIG. 1, a second stem portion 106 is merged with the first stem portion 104, preferably to the section of the first stem portion opposite the section of the first stem portion that extends from the base 102. The second stem portion 106 may be merged with the first stem portion 104 using one of several methods such as, for example, the second stem portion 106 may be affixed to the first stem portion 104 or the first and second stem portions 104, 106 may be integrally molded.

Preferably, the first and second stem portions 104, 106 are rigid. To meet this preferred construction, the stem portions 104, 106 may be made of, for example, a hard plastic. If the probe housing is suited for use, for example, as an intraoperative probe housing, the housing 100 should be suitable for use in a sterile environment, such as in an operating room during surgery.

Figure 6:
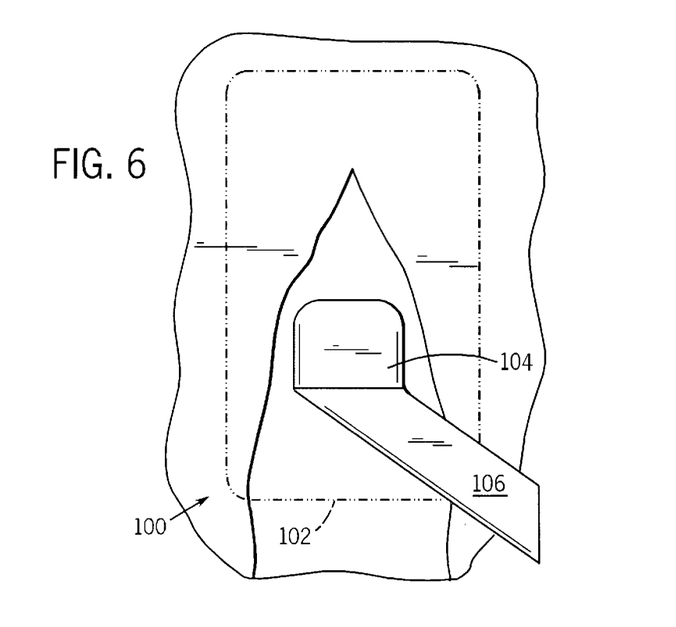
FIG. 6 is a top view of the probe and handle housing being implemented intraoperatively according to a particular embodiment of the present invention.

As shown in FIG. 1A, the first stem portion 104 in this embodiment extends from the base 102 so that the first stem portion 104 extends along a longitudinal axis 110. The longitudinal axis 110 of the first stem portion 104 preferably forms an inclined angle 112 with respect to the longitudinal axis 108 of the base, as shown in FIG. 1A. This relationship between the longitudinal axes of the base 108 and first stem portion 110 permits, for example, the front portion of the base 102 to extend under a portion of unincised skin during an operation, as shown in FIG. 6. A physician may therefore obtain ultrasonic image information about anatomical structures above which the skin has not been cut. This relationship also permits the physician using the probe to be able to more accurately determine the position of the probe relative to the anatomical structure being monitored since the stem portions 104, 106 form a handle for the physician to hold onto the probe during usage. As a result, the physician is able to maintain an accurate sense of direction of the ultrasound beam and its relative position to the anatomical structure the physician is imaging. Additionally, if, for example, the probe handle were to extend from the base at a perpendicular angle (i.e., vertically with respect to the base), the physician's fingers would be more likely to get in the way of the physician's line of sight to the portion of the body being monitored.

As shown in FIG. 1B, the second stem portion 106 is, in the illustrated embodiment, merged with the first stem portion 104 so that the second stem portion 106 extends along a longitudinal axis 114. The longitudinal axis 114 of the second stem portion preferably forms an inclined angle 116 with respect to the longitudinal axis 110 of the first stem portion, as shown in FIG. 1B. This relationship between the first and second stem portions 104, 106 permits the physician using the probe to more accurately determine the position of the probe relative to the anatomical structure being monitored than if only a first stem portion were present. Specifically, the inclined angle 116 permits the physician to accurately maintain the orientation of the probe while viewing, for example, a monitor displaying an output from the probe. The angulation of the second stem portion 106 also allows the physician to hold the probe, at least in part, by the second stem portion 106 without placing his or her fingers in the line of sight to the base of the probe.

Figure 1C:
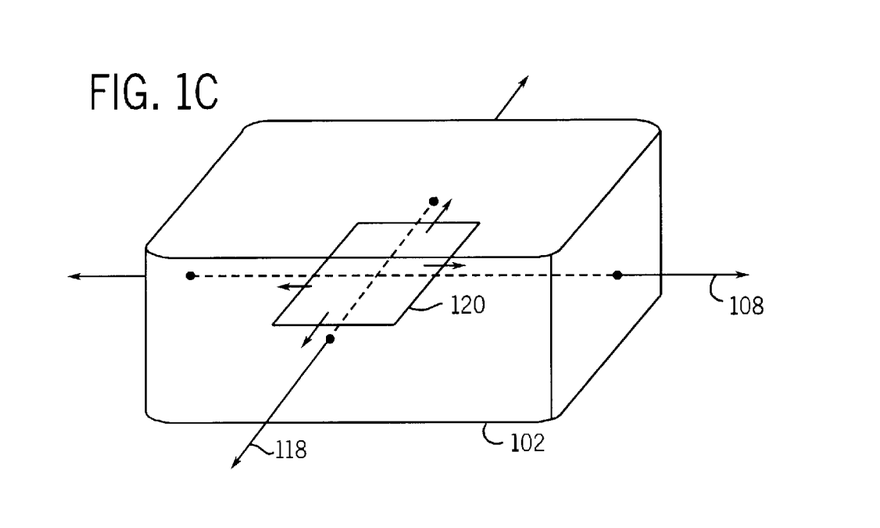
FIG. 1C is a perspective view of the probe and handle housing base.
Figure 2:
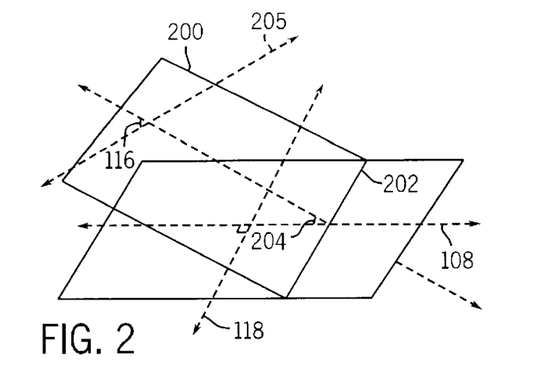
FIG. 2 is a perspective view of the planes in which the axes of the probe and handle housing base, first stem portion, and second stem portion reside.
Figure 3:
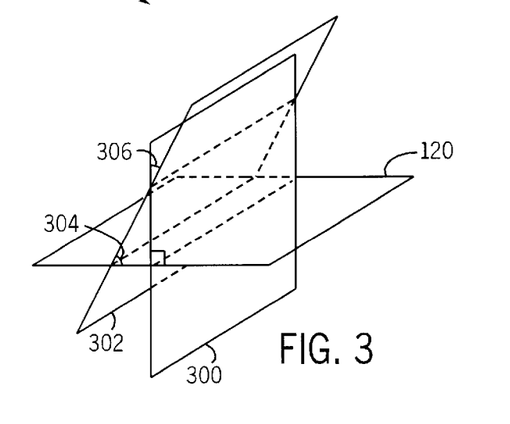
FIG. 3 is a perspective view of the planes in which the axes of the first and second stem portions reside.

Turning now to FIGS. 1C, 2 and 3, FIG. 1C presents the base 102 of the housing 100, including the longitudinal axis of the base 108, the lateral axis of the base 118, and the plane 120 in which the longitudinal and lateral axes may reside. FIG. 2 illustrates the inclined plane 200 in which the first and second stem portions 104, 106 may reside. Also presented are the line of intersection 202 of these two planes, the angle of intersection 204 of these two planes, and the longitudinal axis of the second stem portion 205 (which, in FIG. 2, resides in the inclined plane 200). FIG. 3 presents the planes in which the axes of the base 120, first stem portion 300, and second stem portion 302 may reside.

As shown in FIG. 1C, the base 102 may be constructed such that the lateral 118 and longitudinal 108 axes of the base reside in a first plane 120. Preferably, the first stem axis 104 extends from the base in a second plane 300, shown in FIG. 3, that is substantially perpendicular to the first plane 120, in which the axes of the base 108, 118 reside. This perpendicular relationship between the planes 120, 300 permits the probe to be used in a manner that will cause minimal agitation, including tearing, to an incised portion of the tissue during, for example, intraoperative use, as can be seen from FIG. 6.

In the preferred construction, the second stem portion 106 resides in a third plane 302 that forms an inclined angle 304 with the first plane and an inclined angle 306 with the second plane, as shown in FIG. 3. That is, the second stem portion 106 preferably extends, at least in part, laterally away from the second plane 300 while it extends, at least in part, vertically away from the base 102 of the probe.

In the embodiment illustrated in FIG. 2, the first and second stem portions 104, 106 lie in an inclined plane 200 with respect to the plane 120 in which the longitudinal and lateral axis of the base reside. The inclined plane 200 intersects the first plane 120 along a line 202 parallel to the lateral axis of the base. That is, the first and second stem portions 104, 106 in this embodiment gradually move away from the base at a constant, inclined angle 202, even after the transition from the first stem portion 104 to the second stem portion 106 (shown by angle 116).

Figure 4:
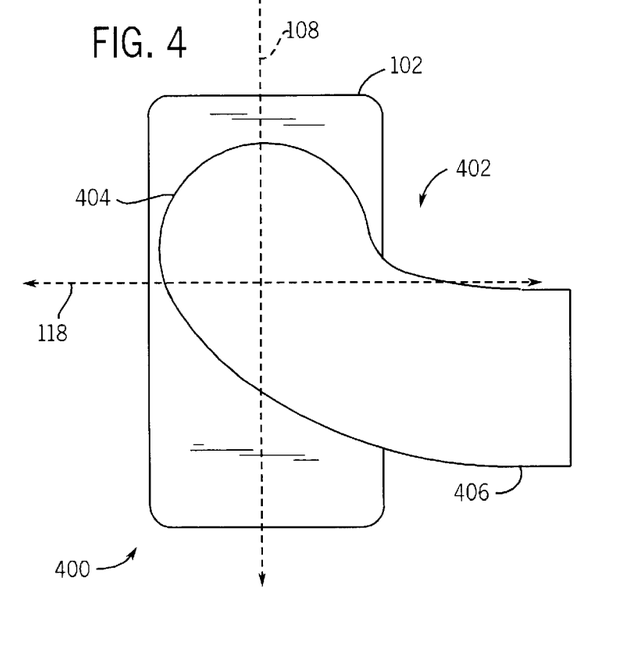
FIG. 4 is a top plan of the probe and handle housing according to an alternative embodiment of the present invention.
Figure 5:
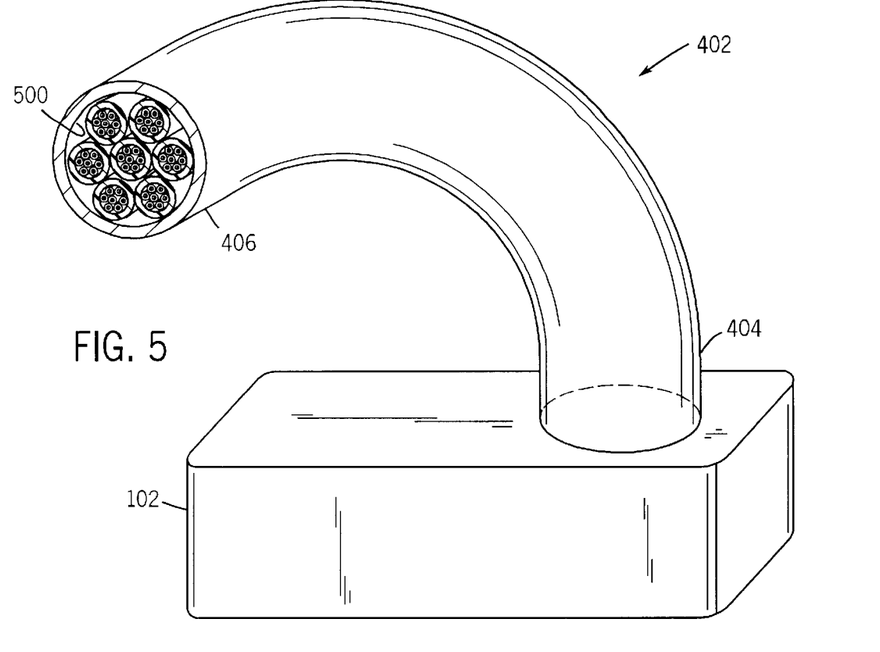
FIG. 5 is a perspective view of the probe and handle housing.

Turning now to FIGS. 4 and 5, those Figures present a probe and handle housing 400 including a base 102 and a handle 402 according to another embodiment of the invention. The illustrated base 102 is elongated and has longitudinal 108 and lateral 118 axes. The handle 402 of the housing 400 has a proximal end 404 and a distal end 406. The proximal end 404 of the handle is coupled to the base 102. The distal end 406 of the handle, however, extends away from the base 102 in a lateral direction with respect to the longitudinal axis 108 of the base. In the illustrated embodiment, the handle 402 is curvilinear in shape and, in fact, forms a continuous curvilinear profile.

As with a previously-referenced embodiment, this shape permits the physician to be able to more accurately determine where the probe is positioned relative to the anatomical structure being imaged. Specifically, if the physician grips the handle 402 near the distal end 406, the physician may have an unobstructed view of the proximal end 404 of the handle and, more importantly, of the base 102 of the probe. Additionally, in the illustrated embodiment of FIG. 5, the handle 402 has a substantially hollow interior 500. The substantially hollow interior 500 permits, for example, the multifilament cable shown in FIG. 5 to lead to a connector suitable for connecting the probe to an ultrasonic diagnostic system which drives the transducer of the probe and receives ultrasonic echo signals from the transducer. The probe cable 107 shown in FIG. 1 may be provided, for example, to contain the multifilament cable.

Preferably, the distal end 406 of the handle extends away from the base 102 at an inclined angle with respect to the base 102. When the probe is used intraoperatively, this shape permits the physician to more easily grip the handle 402 of the probe without agitating or interfering with the incised area of the patient. The probe may also be formed such that the proximal end 404 of the handle extends away from the base 102 at an inclined angle with respect to the base. Preferably, both the proximal 404 and distal 406 ends extend away from the base at an inclined angle. This preferred structure permits as short of a handle 402 as possible while still allowing the physician to properly grip the handle 402 without obstructing the physician's view of the probe.

In the illustrated embodiment of FIG. 4, the longitudinal and lateral axes 108, 118 of the base reside in a first plane 120. The proximal end 404 initially extends from the base 102 in a second plane 300 that is approximately perpendicular to the first plane, as shown in FIG. 3. When used intraoperatively, this illustrated structure permits the handle to extend from the probe in a manner causing minimal agitation of the incised area of the patient, similarly to the embodiment shown in FIG. 6. In the illustrated embodiment, the distal end 406 of the handle lies in an inclined plane that intersects the first plane along a line of intersection that is parallel to the lateral axis of the base; for example, the inclined plane 200 shown in FIG. 2.

Figure 7:
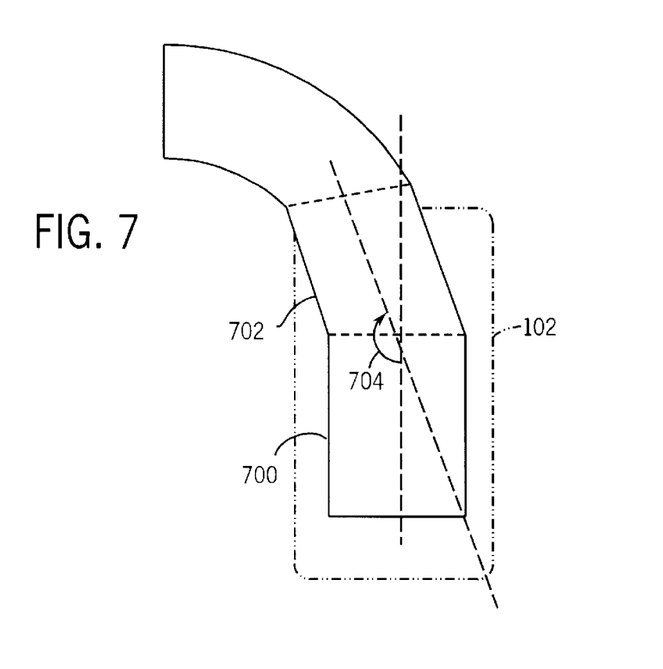
FIG. 7 is a top plan of the probe handle with the probe base shown schematically.

In the present embodiment, the handle 402 may be formed by multiple handle portions, such as the first 700 and second 702 handle portions of FIG. 7, that intersect at an obtuse angle 704. As a result, it can be seen that a handle 402 according to the present invention may be partially curved in shape and partially straight.

Figure 8:
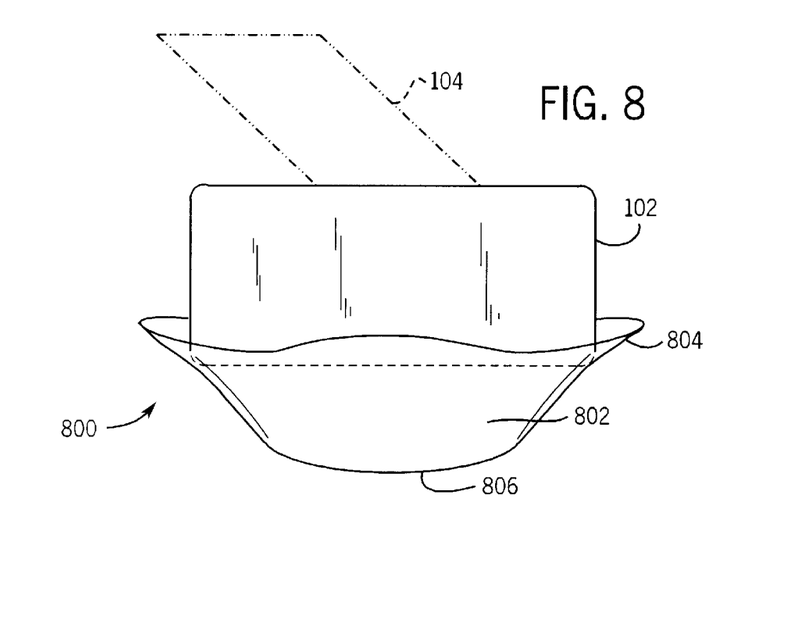
FIG. 8 is a side view of the cushion and probe and handle housing base with the probe stem shown schematically.

According to yet another embodiment of the invention, whichever of the aforementioned configurations is used, a cushion 800 may be removably affixed to the base 102, as shown in FIG. 8. The cushion 800 may be adapted to contain a fluid 802. The fluid 802 contained within the cushion 800 may be composed of a material having a similar sound velocity to anatomical tissue, thereby permitting the ultrasound probe to obtain a better image of the anatomical structure sought to be imaged. Other purposes for the cushion 800 of the present invention will be further discussed below. First, the cushion 800 provides acts as a "pillow" because it provides a damping effect between a pulsing anatomical structure and the probe. The pulsing may be caused by, for example, blood pulsation. Second, the cushion 800 improves the acoustic coupling between a fixed (usually flat) surface of a probe and an often curved and/or irregularly shaped anatomical structure, such as a heart, artery, or other organ. The cushion 800, with the fluid 802 contained therein, is preferably pliable so that the damping and coupling can be effected.

The cushion 800 shown in FIG. 8 is balloon-shaped, having a neck portion 804 and a bag portion 806. Although this shape is not required, when the cushion 800 is so shaped, the neck portion 804 may be removably affixed to the base. In the illustrated embodiment of FIG. 8, the inner perimeter of the neck portion 804 receives the lower surface of the base 102. Preferably, a substantially fluid-impermeable seal is formed where the neck portion 804 is removably affixed to the base 102. Additionally, in the illustrated embodiment, it is the bag portion 806 of the cushion 800 that is adapted to contain a fluid 802.

Whichever of the embodiments is used, however, the handle may also be constructed so that it does not have a substantially hollow interior. The probe cable 107 may exit the handle closer to the base 102 than illustrated in FIG. 1. Alternatively, the probe cable 107 may exit the base 102 separately from the handle (not pictured). The handle may also be removably affixed to the base 102, so that the handle can be detached from the base 102. Moreover, the handle may be formed such that it is flexible and bendable to a user desired shape.

Figure 9:
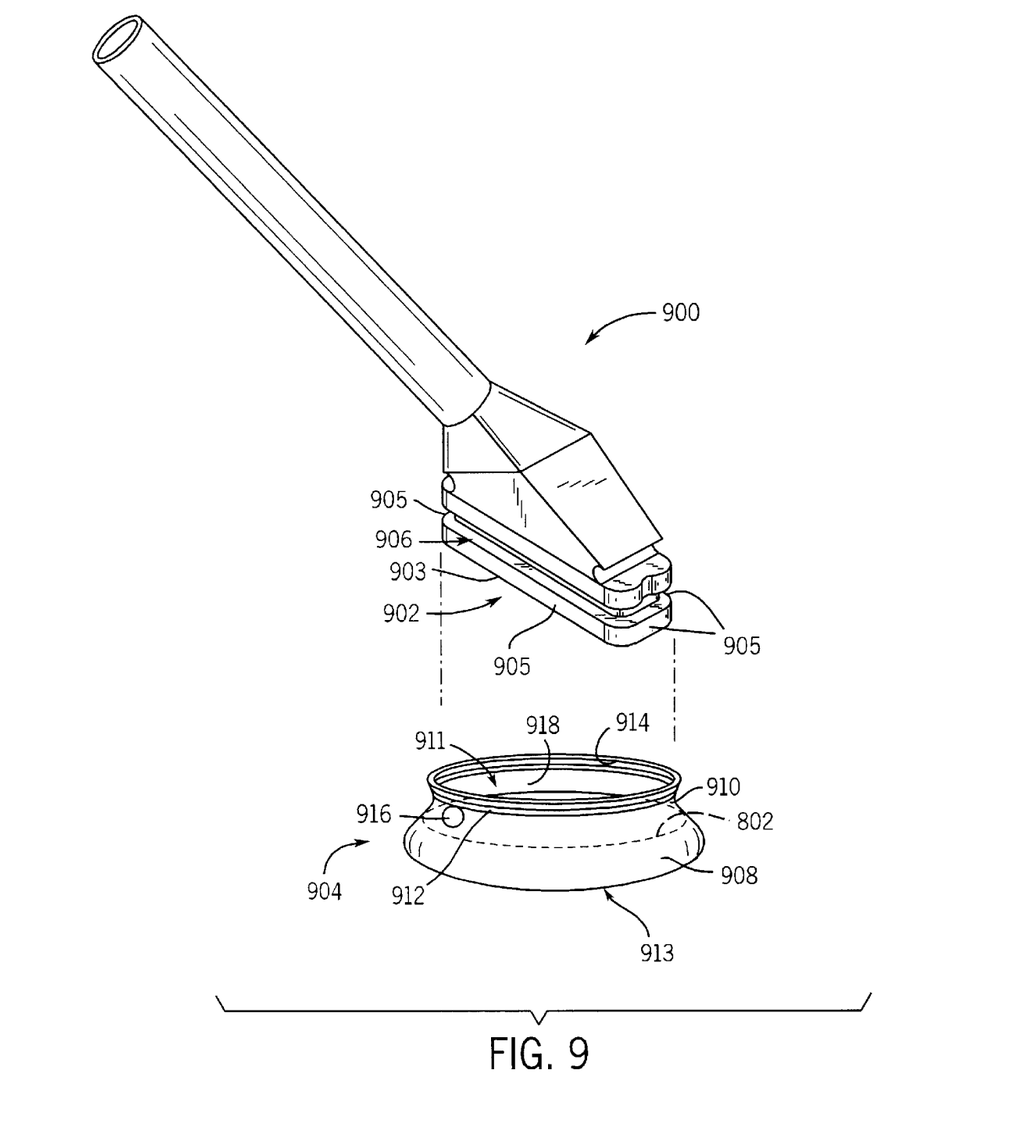
FIG. 9 is a perspective view of an ultrasonic probe and cushion.
Figures 10, 11:
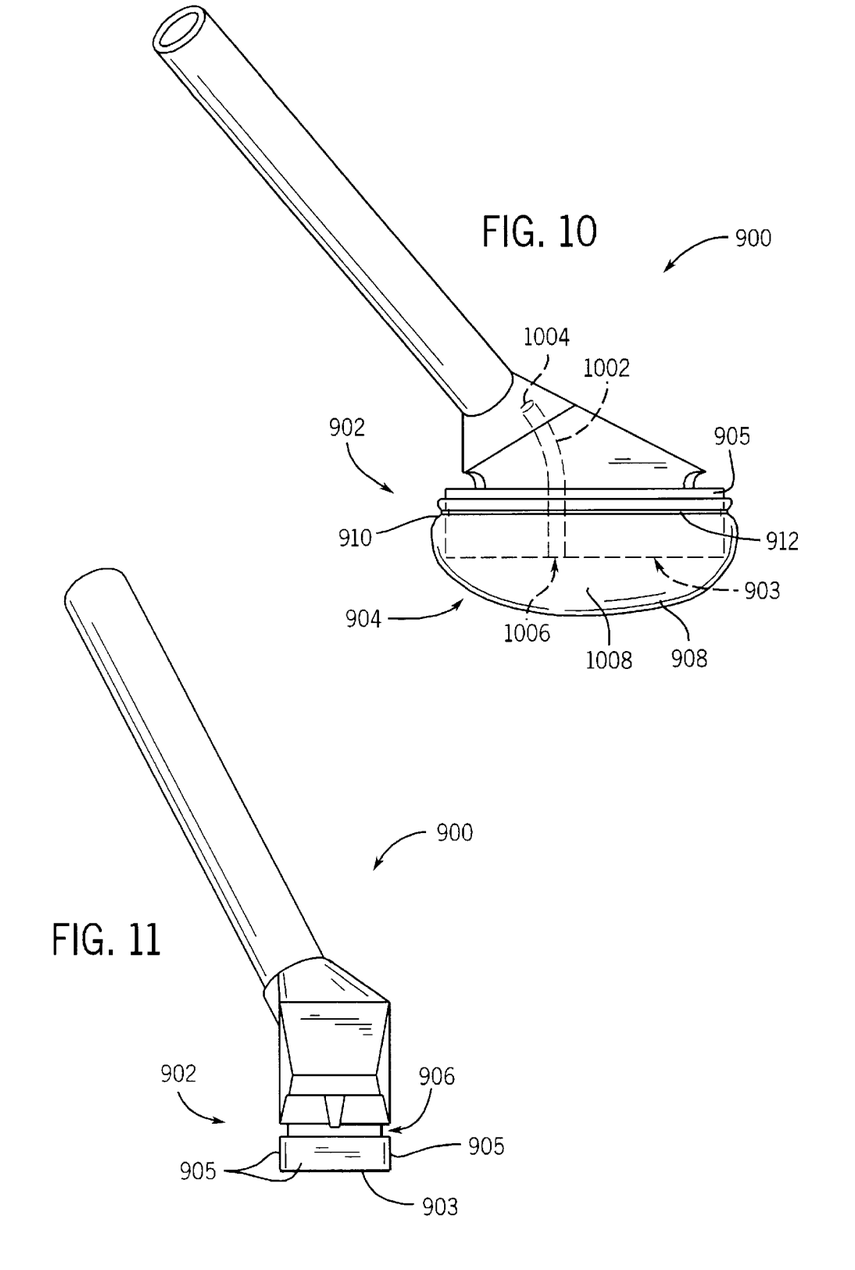
FIG. 10 is a side view of an ultrasonic probe and cushion removably attached to the probe, with the probe shown schematically in part.
FIG. 11 is a front view of an ultrasonic probe and cushion removably attached to the probe, with the probe shown schematically in part.
Figure 17:
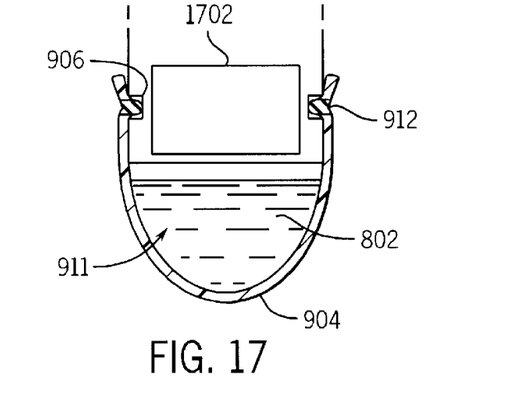
FIG. 17 is a cross-section of a cushion attached to a probe base member according to an alternative embodiment of the present invention.

FIG. 9 illustrates a perspective view of an ultrasonic probe 900 having a base member 902 with an undersurface 903 which houses an ultrasonic transducer 1702 (as illustrated in FIG. 17), and a pliable cushion 904 according to an alternative embodiment of the present invention. The base member 902 is elongated and includes four sidewalls 905. The sidewalls 905 include a groove 906 extending horizontally around the perimeter of the base member 902. The groove 906 is located at an intermediate section of the base member 902, for example approximately one-half way between the undersurface 903 and the top of the base member 902. The perimeter of the illustrated sidewalls 905 is substantially rectangular in shape. FIG. 10 discloses a side view of the probe 900 and cushion 904. FIG. 11 discloses a front view of the probe 900. As shown in FIG. 11, the groove 906 may be a square groove, formed at right angles with respect to the probe base member sidewalls 905.

The illustrated cushion 904 or pad includes a flexible bag portion 908, a neck portion 910, and includes an interior cavity 911. In the preferred embodiment, the cushion 904 includes an elastic member, for example an elastic band 912 as shown in FIG. 9, attached to the neck portion 910 of the cushion 904. The cushion 904 shown in FIG. 9 also includes an undersurface 913 and an aperture 914 through the neck portion 910. FIG. 9 also illustrates an optional fluid receptacle 916 and an inner surface 918 of the cushion 904.

Figure 15:
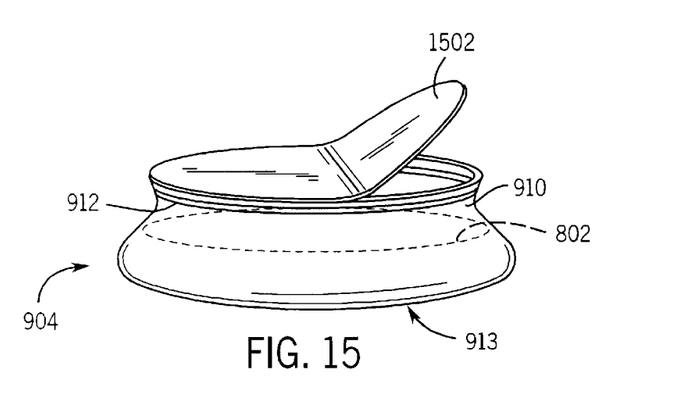
FIG. 15 is a side view of a cushion and peel-away cover according to an alternative embodiment of the present invention.
Figure 16:
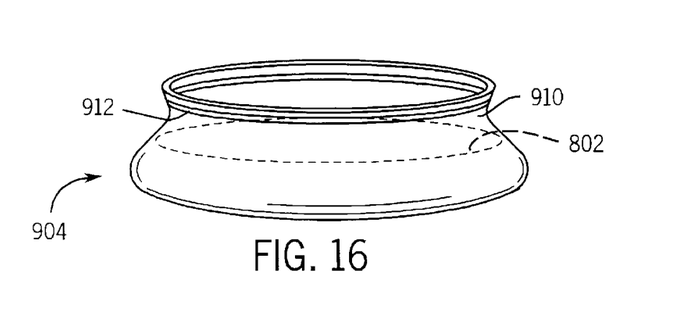
FIG. 16 is a side view of a cushion according to an alternative embodiment of the present invention.

In order to use the ultrasonic probe 900 with the cushion 904, the cushion 904 is filled with a fluid, for example through the aperture 914. Optionally, the cushion 904 may be filled through a resealable fluid receptacle 916 which may allow a needle or similar object to penetrate the cushion 904 to fill the cushion 904 with an acoustic coupling fluid 802. Optionally, the cushion 904 may be filled with a fluid 802 through a tunnel 1002, in the base member 902 and/or other portions of the probe 900, having a receptacle 1004 at one end of the tunnel 1002 for insertion of a fluid, as shown in FIG. 10. In this alternative embodiment, the base member 902 includes on its undersurface 903 an aperture 1006 at the opposite end of the tunnel 1002 for transmitting a fluid 802 to the cushion 904. Optionally, the cushion 904 may be manufactured and shipped containing the fluid 802 and having a peel-away cover 1502 that may be removed prior to use to permit the pad 904 to be secured to the base member 902, as shown in FIG. 15.

Figure 13:
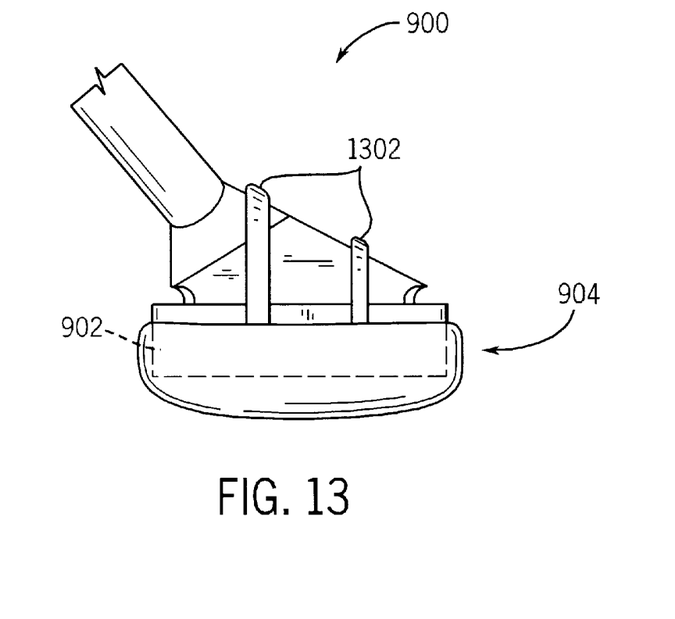
FIG. 13 is a side view of an ultrasonic probe and cushion according to an alternative embodiment of the present invention.
Figure 18:
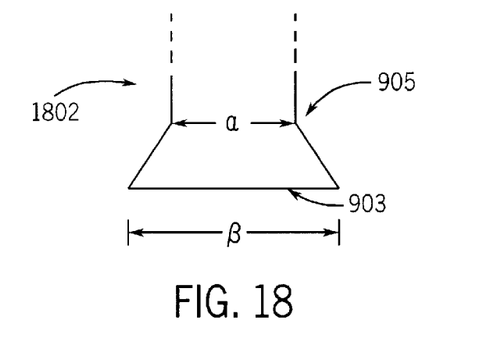
FIGS. 18 and 19 are cross-sections of a probe base member according to alternative embodiments of the present invention.
Figure 19:
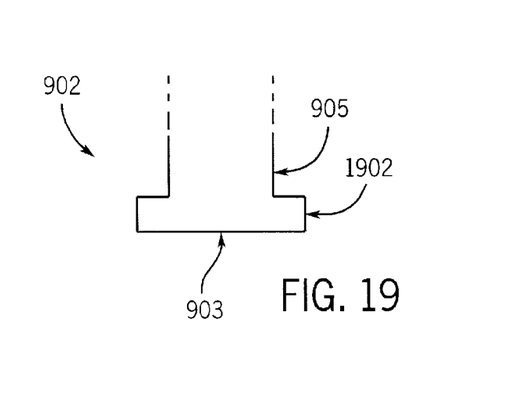

Either before or after the cushion 904 is filled with a fluid 802, the pad 904 is secured to the base member 902 by placing the transducer of the probe 900 through the aperture 914 in contact with the fluid. The elastic band 912 is inserted into the groove 906, as shown in FIGS. 10 and 17. Optionally, the cushion 904 may be secured to the base member 902 by alternate means, for example by tying, clamping or strapping the cushion 904 to the base member 902. For example, as shown in FIG. 13, the cushion 904 is strapped to the probe 900 by one or more straps 1302. In the embodiment illustrated by FIG. 13, the cushion 904 may also be equipped with an additional device for maintaining a fluid-impermeable seal with the base member 902. Optionally, the cushion 904 may be made from an elastic material and the cushion 904 may be secured to the probe 900 simply by stretching the neck portion 910 of the pad 904 around the base member 902, as shown in FIG. 8. Optionally, the sidewalls 905 of the base member 902 may be shaped to form a trapezoid, step or other structure for securing the cushion 902 to the probe 900. FIG. 18 illustrates a trapezoidal shaped base member 1802, which includes an upper cross-section α and a lower long cross-section β to assist in retaining a cushion 904 to the base member 902. FIG. 19 illustrates a square step 1902 along the base of the sidewall 902 to assist in retaining a cushion 904 to the base member 902.

The cushion 904 may be made of any one or more of a number of pliable materials. Preferably, the material should be able to retain a fluid and be able to stretch to fit around the perimeter of the base member. The material preferably has acoustical qualities such that it does not substantially interfere with the transmitted and received ultrasonic waves. Exemplary materials include latex, vinyl, nitrile and ELASTYREN®. ELASTYREN® is a substitute for latex for those who are allergic to latex and is manufactured by ECI Medical Technologies, Inc. in Bridgewater, Nova Scotia, Canada.

Figure 14:
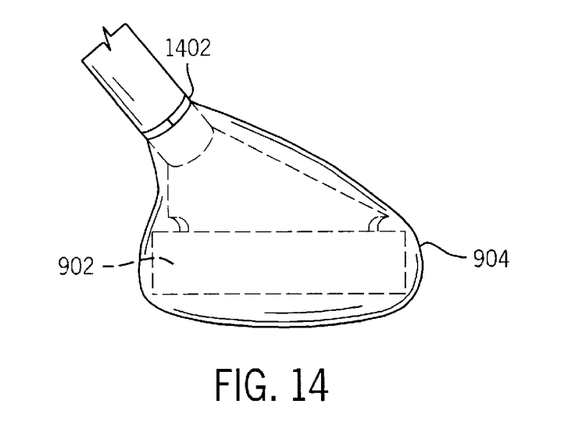
FIG. 14 is a side view of an ultrasonic probe and cushion according to an alternative embodiment of the present invention.

The cushion 904 may be removably affixed to the base, as shown in FIGS. 8, 10 and 11. A fluid compartment 908 is created between the bottom surface 903 of the base member 902 and the inner surface 918 of the cushion 904. Optionally, the cushion 904 may envelop the entire base member 902 and a portion of the stem, as shown in FIG. 14. The cushion 904 may be secured to the probe stem by using a strap 1402, for example a VELCRO® strap. Preferably, the fluid contained within the cushion 904 is composed of a material having a similar sound velocity to anatomical tissue (or at least a sound velocity that does not adversely affect the ultrasonic waves). This permits the ultrasound probe 900 to obtain a better image of the anatomical structure sought to be imaged. The illustrated cushion 904 can be filled with sterile water or a gel. Sterile water is preferred because the preferred cushion 904, when filled immediately prior to usage, does not need to be shipped and stored while containing a fluid (and therefore is not susceptible to evaporation). The use of water instead of gel is beneficial because water has a sound velocity that is more similar to anatomical tissue than are gels.

During use, the cushion 904 acts as a pillow or cushion to dampen forces and motion external to the probe, such as during intraoperative use. Such external forces may include pulsing anatomical structures, for example the heart, other organs or other tissue related to the pressure side of the blood system. External forces or motion may also include motion during muscle activation. The cushion 904 also improves the acoustical coupling between a fixed surface of the base member 902 and an often curved and/or irregularly shaped anatomical structure, such as a heart, artery, or other organ. Specifically, the cushion 904 conforms to the shape of the anatomical tissue, thereby eliminating air pockets between the probe 900 and tissue and improving the ultrasound image quality. Without the pliable cushion 904, the rigid undersurface 903 of the illustrated base member 902 might deform the organ and/or its blood flow when pressed against the organ, thereby adversely affecting ultrasound image quality. For this reason, the cushion 904, with the fluid 802 contained therein, is preferably pliable so that the damping and coupling can be effected. During use, the undersurface 913 of the cushion 904 may contact the anatomic structure sought to be imaged. The pliable cushion 904 will deform according to the pressure placed on the pad by the organ, thus compensating for the movement of the organ and the probe 900 while still obtaining an acoustic coupling for the ultrasound energy.

The cushion 904 shown in FIGS. 8, 9 and 10 is balloon-shaped, having a neck portion 910 and a bag portion 908. Although this shape is not required, when the cushion 904 is so shaped, the neck portion 910 may be removably affixed to the base 902, for example as discussed above. In the illustrated embodiment of FIG. 8, the inner perimeter of the neck portion 910 receives the lower surface of the base 902, and thus no elastic member is needed. Preferably, a substantially fluid-impermeable seal is formed where the neck portion 910 is removably affixed to the base 902, regardless of whether an elastic member is used. Additionally, in the illustrated embodiment of FIG. 8, it is the bag portion of the cushion pad 904 that is adapted to contain a fluid 802. Optionally, the cushion 904 may contain a sealing member 1602 on the interior 911 of the cushion 904 below the neck portion 910 of the cushion 904. If a sealing member 1602 is used, the undersurface 903 of the base member 902 is preferably placed in direct contact with the sealing member 1602 during use (to avoid the existence of air pockets between the base member 902 and the anatomic structure).

Figure 12:
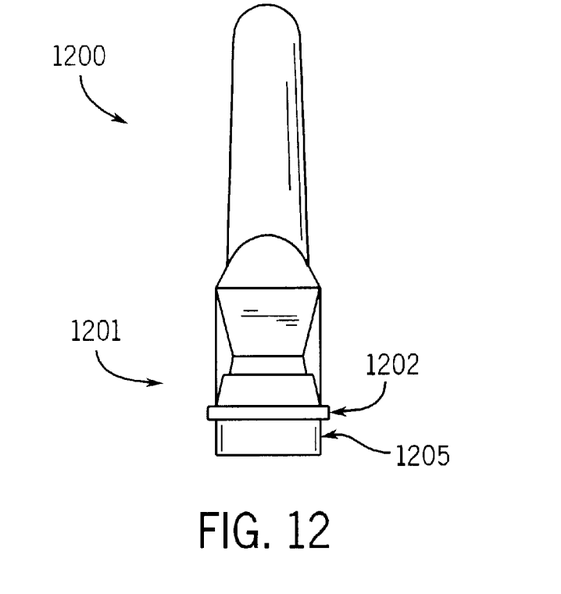
FIG. 12 is a front view of the ultrasonic probe and cushion according to an alternative embodiment of the present invention.

Turning now to FIG. 12, that Figure presents an alternative embodiment of an ultrasound probe 1200 wherein the base member 1201 includes a ridge 1202 for securing a cushion 904 to the base member 1201. The ridge 1202 may be used for affixation of a pliable cushion 904 having an elastic member to the base member 1201. Optionally, a pliable pad may have a rigid ring at its neck portion shaped to form a snap fit with the ridge 1202.

While particular embodiments of the invention have been shown, it will be understood, of course, that the invention is not limited thereto since modifications may be made by those skilled in the art, particularly in light of the foregoing teachings. For example, although the invention is at times discussed as being used intraoperatively, the invention is not limited to intraoperative probes. Moreover, although the invention is shown in FIGS. 9–11 as having a multi-angled handle, the one of many different types of handles invention is not limited thereto since it may be used with an ultrasound probe having one of many type of handle, for example as indicated in FIGS. 8 and 12. It is, therefore, contemplated that the appended claims will cover any such modifications as incorporate those features which constitute the essential features of these improvements within the true spirit and the scope of the invention.

What is claimed is:

1. An ultrasonic probe for scanning an anatomical structure, comprising:
   a base member;
   an ultrasonic transducer housed by said base member; and
   an intermediary damping member secured to said base member, said damping member absorbing relative motion between said base member and a dynamic anatomical structure contacting said damping member, said damping member having an interior cavity for receiving an acoustic coupling fluid.

2. The probe of claim 1 wherein said damping member has a pliable anatomic structure contacting surface for contacting anatomical tissue during use.

3. The probe of claim 1 wherein said probe is especially suited for intraoperative use.

4. The probe of claim 1 wherein said base member includes an undersurface and said undersurface and said interior cavity define a chamber for receiving the acoustic coupling fluid.

5. The probe of claim 1 wherein said base member comprises an undersurface and said damping member is located alongside said undersurface.

6. The probe of claim 5 wherein said damping member abuts said undersurface.

7. The probe of claim 1 wherein said damping member is directly secured to a periphery of said base member.

8. The probe of claim 1, wherein said base member comprises a peripheral groove for securing said intermediary damping member to said base member.

9. The probe of claim 1 wherein said damping member is made of one pliable material and includes an elastic band having an aperture therethrough, said elastic band securely engaging said base member.

10. The probe of claim 1 wherein said damping member is directly secured to said base member.

11. The probe of claim 1 wherein said damping member absorbs relative motion caused by motion of the heart.

12. The probe of claim 1, wherein said damping member absorbs relative motion between said base member and the dynamic anatomical structure due to pulsation of blood flow from, to or through the heart.

13. An ultrasonic probe which is particularly suitable for intraoperative use while scanning an anatomical structure, comprising:
   a base member;
   an ultrasonic transducer housed by said base member; and
   a flexible intermediary buffer damping external forces caused by a dynamic anatomical structure, said buffer having an interior cavity for receiving an acoustic coupling fluid and having an opening in one side of said buffer, said base member being removably secured to said opening.

14. The probe of claim 13 wherein said buffer includes an elastic member and said base member includes a peripheral groove for receiving said elastic member, said groove extending substantially horizontally along at least one sidewall of said base member.

15. The probe of claim 14 wherein said groove comprises a substantially square cross-section.

16. The probe of claim 13 wherein said base member includes sidewalls having a peripheral groove running substantially the entire perimeter of said sidewalls.

17. The probe of claim 13 wherein said flexible intermediary buffer conforms to a contour of the anatomical structure being scanned to maintain an effective coupling contact with the anatomical structure.

18. The probe of claim 13 wherein said base member includes four sidewalls and defines a substantially rectangular shape.

19. The probe of claim 13 wherein said intermediary buffer forms a substantially fluid-impermeable seal when said intermediary buffer is affixed to said base by said elastic member.

20. The probe of claim 13 wherein said intermediary buffer entirely houses said base member.

21. The probe of claim 13 wherein said buffer includes an elastic member about said opening and said base member includes a ridge, said elastic member and base member cooperating to secure said buffer to said base member, said ridge extending substantially horizontally along at least one sidewall of said base member.

22. The probe of claim 13 wherein said flexible intermediary buffer is made of one pliable material and includes an elastic band having an aperture therethrough, said elastic band securely engaging said base member.

23. The probe of claim 13 wherein said flexible intermediary buffer absorbs relative motion caused by motion of the heart.

24. An ultrasonic probe for scanning an anatomical structure, comprising:

a base member;

an ultrasonic transducer mounted in said base member; and a flexible coupling member damping external forces caused by a dynamic anatomical structure, said coupling member being secured to said base member, and having an interior cavity for receiving an acoustic coupling fluid and a malleable undersurface adapted to contact, and conform to, the dynamic anatomical structure.

25. An ultrasound probe comprising:

a transducer housing;

an ultrasonic transducer mounted in said transducer housing; and a flexible cushioned pad directly secured to a periphery of said transducer housing damping external forces caused by a dynamic anatomical structure.

26. The probe of claim 25 wherein said cushioned pad is removably affixed to said transducer housing.

27. The probe of claim 25 further comprising an elastic member for securing said cushioned pad to said transducer housing.

28. The probe of claim 25 wherein said cushioned pad includes an aperture for receiving a fluid.

29. The probe of claim 25 wherein said transducer housing includes a bottom surface and said cushioned pad is removably affixed to said bottom surface.

30. The probe of claim 25, wherein the housing includes a channel therethrough with a first opening in communication with a cavity formed between said cushioned pad and the transducer and a second opening to accept a coupling medium.

31. The probe of claim 25 wherein said transducer housing comprises a peripheral groove for securing said flexible cushioned pad to said transducer housing.

32. The probe of claim 25 wherein said flexible cushioned pad is made of one pliable material and includes an elastic band having an aperture therethrough, said elastic band securely engaging said transducer housing.

33. The probe of claim 25 wherein said flexible cushioned pad is directly secured to said transducer housing.

34. The probe of claim 25 wherein said flexible cushioned pad absorbs relative motion caused by motion of the heart.

35. The probe of claim 25, wherein said flexible coupling member damps forces caused by a dynamic anatomical structure due to pulsation of blood flow from, to or through the heart.

36. An intermediary member for use with an ultrasound probe, the intermediary member being located between the probe and an anatomical structure to be analyzed, the intermediary member comprising:

a flexible region adapted to contact a dynamic anatomical structure, said flexible region damping external forces caused by the dynamic anatomical structure, said flexible region substantially conforming to a contour of the anatomical structure;

a probe-mounting segment adapted to be securely affixed to a probe in communication with said flexible region; and a body located between said flexible region and said probe-mounting segment to define an interior void adapted to receive an acoustic medium.

37. The intermediary member of claim 36, wherein said probe-mounting segment includes an opening adapted to accept the ultrasound probe, said opening being sealed, before attaching the intermediary member to the probe, with a removable cover.

38. The intermediary member of claim 37, wherein said flexible region, probe-mounting segment and body form a hermetically sealed cavity containing an acoustic coupling medium.

39. The probe of claim 36, wherein said flexible region damps forces caused by the dynamic anatomical structure due to pulsation of blood flow from, to or through the heart.

* * * * *